US009730583B2

(12) United States Patent
Kiderman et al.

(10) Patent No.: US 9,730,583 B2
(45) Date of Patent: *Aug. 15, 2017

(54) METHOD FOR OBJECTIVE DIAGNOSTICS OF INTERNUCLEAR OPTHALMOPLIGIA, OCULAR LATERAL PULSION, PROGRESSIVE SUPERNUCLEAR PALSY AND GLISSADES EYE MOVEMENTS

(71) Applicant: Neuro Kinetics, Inc., Pittsburgh, PA (US)

(72) Inventors: Alexander D Kiderman, Pittsburgh, PA (US); Yakov Eydelman, Pittsburgh, PA (US); Terri Evelyn Ives, Littleton, CO (US)

(73) Assignee: NEURO KINETICS, INC, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/819,643

(22) Filed: Aug. 6, 2015

(65) Prior Publication Data
US 2015/0335240 A1 Nov. 26, 2015

Related U.S. Application Data

(63) Continuation of application No. 14/320,613, filed on Jun. 30, 2014, now Pat. No. 9,107,616, which is a (Continued)

(51) Int. Cl.
A61B 3/14 (2006.01)
A61B 3/113 (2006.01)
(Continued)

(52) U.S. Cl.
CPC ............ A61B 3/113 (2013.01); A61B 3/0025 (2013.01); A61B 3/0041 (2013.01);
(Continued)

(58) Field of Classification Search
CPC ......... A61B 3/113; A61B 3/0025; A61B 3/14; A61B 3/145; A61B 3/112; A61B 3/0091;
(Continued)

(56) References Cited

U.S. PATENT DOCUMENTS 5,422,690 A 6/1995 Rothberg et al.
7,071,831 B2 7/2006 Johns
(Continued)

OTHER PUBLICATIONS

K. M. Sharika, Arjun Ramakrishnan and Aditya Murthy, Control of Predictive Error Correction During a Saccadic Double-StepTask, http//jn.physiology.org/cgi/content/full/10015/2757, National Brain Research Centre, Nainwal More, Manesar, Haryana, India, J Neurophysiology. Nov. 2008;100(5):2757-70. Epub Sep. 24, 2008.*
(Continued)

Primary Examiner — Thomas K Pham
Assistant Examiner — Sharrief Broome
(74) Attorney, Agent, or Firm — Blynn L. Shideler; Krisanne Shideler; BLK Law Group

(57) ABSTRACT

A video oculography (VOG) system for calculation and display of Corrective Secondary Saccades Analysis is disclosed and utilized in a method for Objective Diagnostics of Internuclear Opthalmopligia, Ocular Lateral Pulsion, Progressive Supernuclear Palsy and Glissades. The method comprises the steps of using a VOG system to calculate corrective saccades. The VOG based system is configured to collect eye images of the patient in excess of 60 hz and configured to resolve eye movements smaller than at least 3 degrees of motion and collects eye movement data wherein at least one fixation target is presented to the subject in a defined position configured to yield a voluntary saccadic eye response from at least one eye of the patient. The latency, amplitude, accuracy and velocity of each respective corrective saccade and totals latency and accuracy are calculated.

20 Claims, 4 Drawing Sheets

Related U.S. Application Data continuation of application No. 13/080,981, filed on Apr. 6, 2011, now Pat. No. 8,764,193, which is a continuation of application No. PCT/US2009/059749, filed on Oct. 6, 2009.

(60) Provisional application No. 61/102,924, filed on Oct. 6, 2008.

(51) Int. Cl.
*A61B 3/00* (2006.01)
*A61B 5/00* (2006.01)

(52) U.S. Cl.
CPC ............ *A61B 3/0091* (2013.01); *A61B 3/145* (2013.01); *A61B 5/4076* (2013.01); *A61B 5/4863* (2013.01); *A61B 5/6814* (2013.01); *G03B 2213/025* (2013.01)

(58) Field of Classification Search
CPC ........... A61B 3/0041; A61B 3/00; A61B 3/10; A61B 5/4863; A61B 3/0008; A61B 3/02; A61B 5/0496; A61B 5/16; A61B 3/102; A61B 5/168; A61B 3/005; A61B 3/024
USPC .................................................. 351/210–221
See application file for complete search history.

(56) References Cited

U.S. PATENT DOCUMENTS

| | | |
|---|---|---|
| 8,568,311 B2 | 10/2013 | LaPlaca et al. |
| 8,764,193 B2 | 7/2014 | Kiderman |
| 9,107,616 B2 | 8/2015 | Kiderman |
| 2002/0099305 A1 | 7/2002 | Fukushima et al. |
| 2004/0039066 A1 | 2/2004 | Crea |
| 2005/0099601 A1 | 5/2005 | MacDougall et al. |
| 2006/0176448 A1 | 8/2006 | Van de Velde |
| 2006/0203197 A1 | 9/2006 | Marshall |
| 2006/0270945 A1 | 11/2006 | Ghajar |
| 2006/0279698 A1 | 12/2006 | Muhlhoff et al. |
| 2007/0132841 A1 | 6/2007 | MacDougall et al. |
| 2007/0177103 A1 | 8/2007 | Migliaccio et al. |
| 2007/0291232 A1 | 12/2007 | Marshall |
| 2008/0049186 A1 | 2/2008 | MacDougall et al. |
| 2008/0049187 A1 | 2/2008 | Joos et al. |
| 2008/0242949 A1* | 10/2008 | Jung ................... A61B 5/1101 600/300 |

OTHER PUBLICATIONS

Rascol, O., Clanet, M., Montastruc, J.L., Simonetta, M., Soulier-Esteve, M.J., Doyon, B., Rascol, A., Abnormal Ocular Movements in Parkinson's Disease, Evidence for Involvement of Dopaminergic Systems, Dec. 1998, from the Department of Medical and Clinical Pharmacology ( NSERM U317) pp. 1193-1212.*

Niestroy, Neuro-ophthalmologic aspects of multiple sclerosis: Using eye movements as a clinical and experimental tool, Clinical Ophthalmology 2007:1(3) 267-272.*

Dr. Timothy C. Hain, Saccade Tests, http://www.dizziness-and-balance.com/practice/saccades/saccade.htm, Apr. 29, 2011.

K. M. Sharika, Arjun Ramakrishnan and Aditya Murthy, Control of Predictive Error Correction During a Saccadic Double-Step Task, http://jn.physiology.org/cgi/content/full/100/5/2757, National Brain Research Centre, Nainwal More, Manesar, Haryana, India, J Neurophysiol. Nov. 2008;100(5):2757-70. Epub Sep. 24, 2008.

Deubel H, Wolf W, Hauske G, Abstract of: Corrective Saccades: Effect of Shifting the Saccade Goal, Vision Res. 1982;22(3):353-64, PMID: 7090189 [PubMed—indexed for Medline].

Rascol, O., Clanet, M., Montastruc, J.L., Simonetta, M., Soulier-Esteve, M.J., Doyon, B., Rascol, A., Abnormal Ocular Movements in Parkinson's Disease, Evidence for Involvement of Dopaminergic Systems, Dec. 1998, From the Department of Medical and Clinical Pharmacology (INSERM U317) pp. 1193-1212.

* cited by examiner

METHOD FOR OBJECTIVE DIAGNOSTICS OF INTERNUCLEAR OPTHALMOPLIGIA, OCULAR LATERAL PULSION, PROGRESSIVE SUPERNUCLEAR PALSY AND GLISSADES EYE MOVEMENTS

RELATED APPLICATIONS

The present application is a continuation of U.S. patent application Ser. No. 14/320,613 filed Jun. 30, 2014, published Nov. 6, 2014 as Publication Number 2014/0327881, which is incorporated herein by reference, and which issued Aug. 18, 2015 as U.S. Pat. No. 9,107,616, which is incorporated herein by reference.

U.S. patent application Ser. No. 14/320,613 is a continuation of Ser. No. 13/080,981 filed Apr. 6, 2011, published Apr. 5, 2012 as Publication Number 2012/0081666, which is incorporated herein by reference, and which issued Jul. 1, 2014 as U.S. Pat. No. 8,764,193, which is incorporated herein by reference.

U.S. patent application Ser. No. 13/080,981 claims the benefit of International Patent Application Serial Number PCT/US09/59749 filed Oct. 6, 2009 and published as WO-2010/042557, which is incorporated herein by reference.

International Patent Application Serial Number PCT/US09/59749 claims the benefit of U.S. provisional application Ser. No. 61/102,294, entitled "Method and Apparatus for Corrective Secondary Saccades Analysis with Video Oculography System and Method for Objective Diagnostics of Internuclear Opthalmopligia, Ocular Lateral Pulsion, Progressive Supernuclear Palsy and Glissades Eye Movements" filed Oct. 6, 2008.

BACKGROUND OF THE INVENTION

1. Field of the Invention

The present invention relates to a method of using a portable, modular VOG system that provides for the calculation and display of saccade eye movement for objective analysis.

2. Background Information

The present invention relates to Video-oculography, also called VOG, and video-oculographic recording of eye movement has been shown to be a highly effective non-invasive technology for evaluating eye movement. See the Richard E. Gans article in the May 2001, volume 54, pages 40-42 of The Hearing Journal, which provide great insight to the beginning of practical goggle based VOG systems in 2001. As a historical note, for over 50 years, clinicians and researchers have depended upon electronystagmography (ENG or EOG) to evaluate peripheral and central vestibular function. Although ENG/EOG remains in significant use, the need to place electrodes around the eyes and the inability to record or observe a torsional nystagmus have represented significant limitations with this technology. Another drawback is that much of the testing must be performed with the patient's eyes closed. Therefore, clinicians and researchers have been dependent on the graphic, uni-dimensional recording to speculate as to what movement the eyes were actually making beneath closed eyelids.

Abnormalities of eye movement provide valuable information about the location of the dysfunction or disease process. Many abnormalities are specific to certain pathophysiology or pharmacologic influences. The advantage of recording/evaluating eye movements versus other axial or limb musculature is that they are easier to interpret. Eye movement is limited to movement in three planes: horizontal, vertical, and rotational. Pupil dilation represents another parameter that may be desired to be tracked for certain applications.

Eye movements may be categorized as those that stabilize vision during head movement and those that shift vision. The vestibular system stabilizes vision with head movement through the mechanoreceptors of the labyrinth, sensing the direction and speed of head acceleration and moving the eyes accordingly. When disease affects a particular semicircular canal within the labyrinth, nystagmus may occur in the plane of the involved canal. It is this anatomical and physiological relationship of the VOR that makes new technologic improvements in its assessment so important.

Current VOG systems that accurately track eye movement for diagnostic purposes can be represented by those described in U.S. Patent Application Publications 2005-0099601, 2007-0177103, 2007-0132841, 2008-0049186, and 2008-0049187 which are incorporated herein by reference. A further example of a current state of the art VOG system include the 2008 I-Portal™ brand VOG systems from Neuro-Kinetics, Inc, which is a fully digital VOG system that delivers accurate 4D eye tracking. The lightweight goggle system is offered in standard 60 Hz and high-speed 120 Hz goggle sets, both occluded and free field of view. Higher speeds are available in customized applications with the integration of higher speed cameras, with the system currently accommodating up to 5000 hz cameras.

A saccade, for the purpose of this application, is a fast movement of an eye. Eye saccades are generally quick, simultaneous movements of both eyes in the same direction. Saccades serve as a mechanism for fixation, rapid eye movement, and the fast phase of optokinetic nystagmus. Humans, and other animals, do not look at a scene in a steady way. Instead, the eyes move around, locating interesting parts of the scene and building up a mental 'map' corresponding to the scene. One reason for saccades of the human eye is that the central part of the retina, the fovea, plays a critical role in resolving objects. By moving the eye so that small parts of a scene can be sensed with greater resolution, body resources can be used more efficiently.

In addition, the human eye is in a constant state of vibration, oscillating back and forth at a rate of about 30-70 Hz. These "micro-saccades" are tiny movements, roughly 20 arcseconds in excursion and are generally imperceptible. They serve to refresh the image being cast onto the rod cells and cone cells at the back of the eye. Without microsaccades, staring fixedly at something would cause the vision to cease after a few seconds since rods and cones only respond to a change in luminance.

Saccades are the fastest movements produced by the human body. The peak angular speed of the eye during a saccade reaches up to 1000°/sec in monkeys and somewhat less in humans. Saccades to an unexpected stimulus normally take about 200 milliseconds to initiate and then last from about 20 to 200 milliseconds, depending on their amplitude. The amplitude of a saccade is the angular distance that the eye travels during the movement. For amplitudes up to about 60 degrees, the velocity of a saccade linearly depends on the amplitude (the so called "saccadic main sequence"). For instance, a 10° amplitude is associated with a velocity of 300°/sec, and 30° is associated with 500°/sec. In saccades larger than 60 degrees, the peak velocity starts to plateau (non-linearly) toward the maximum velocity attainable by the eye.

Saccades may rotate the eyes horizontally or vertically, or in any oblique direction to change gaze direction (the direction of sight that corresponds to the fovea), but normally saccades do not rotate the eyes torsionally. Torsion can be defined as clockwise or counterclockwise rotation around the line of sight when the eye is at its central primary position. Head-fixed saccades can have amplitudes of up to 90° (from one edge of the oculomotor range to the other), but in normal conditions saccades are far smaller, and any shift of gaze larger than about 20° is accompanied by a head movement. During such gaze saccades, first the eye produces a saccade to get gaze on target, whereas the head follows more slowly and the vestibulo-ocular reflex causes the eyes to roll back in the head to keep gaze on the target.

There are many, some rare, abnormalities of eye movements that can be diagnosed through observation of saccades eye movements. See, for reference, Saccade Calibration Testing article by Dr. Timothy C. Hain at http://www.dizziness-and-balance.com/practice/saccade.htm, which discusses i: Disorders of Saccade velocity (Too slow and Too fast), ii) Disorders of latency (timing), iii) Disorders of Saccades Accuracy (Overshoot, Undershoot, Blindness, Glissades and Pulsion), and iv) Disorders with "Square Wave Jerks" (saccadic oscillations with a latency between each saccade). This background is believed to be known to one of ordinary skill in the art associated with the present claimed invention.

Microsaccades are a kind of fixational eye movement. They are small, jerk-like, involuntary eye movements, similar to miniature versions of voluntary saccades. They typically occur during prolonged visual fixation (of at least several seconds). Microsaccade amplitudes vary from 2 to 120 arcminutes. The role of microsaccades in visual perception has been a debated topic which, currently, is unresolved. It has been proposed that microsaccades correct displacements in eye position produced by drifts, although non-corrective microsaccades also occur. Microsaccades were also believed to prevent the retinal image from fading, but they do not occur often enough for that purpose, considering that perfectly stabilized images can disappear from perception in a few seconds or less. The current consensus is that all fixational eye movements are important for the maintenance of visibility.

The present application deals with secondary, and higher order, corrective saccades which may be considered as micro-saccades, namely corrective micro-saccades, following a main or primary saccade eye movement.

There remains a need in the art for a simple, and simple to use, VOG system effective for clinical and research applications.

SUMMARY OF THE INVENTION

Some of the above objects are achieved with a goggle based VOG system that calculates, and displays secondary, and higher, corrective saccades. A method of measuring ocular response in a subject comprising the steps of: A) Providing a video oculography based system for the subject with the video oculograpghy system configured to collect eye images of the patient in excess of 60 hz and configured to resolve eye movements smaller than at least 3 degrees of motion; B) Collecting eye data with the video oculography based system wherein at least one fixation target is presented to the subject in a defined position configured to yield a voluntary saccadic eye response from at least one eye of the patient; and C) Calculating corrective saccade measurements from the eye data including at least one of: i) total number of corrective saccades associated with the subject's eye movement to each fixation target presented to the subject; ii) first corrective saccade latency associated with the subject's first corrective saccade eye movement to each fixation target presented to the subject; iii) first corrective saccade amplitude associated with the subjects first corrective saccade eye movement to each fixation target presented to the subject; iv) first corrective saccade accuracy associated with the subject's first corrective saccade eye movement to each fixation target presented to the subject; v) first corrective saccade velocity associated with the subjects first corrective saccade eye movement to each fixation target presented to the subject; vi) ratio of first corrective saccade amplitude to main saccade amplitude associated with the subject's eye movement to each fixation target presented to the subject; and vii) ratio of total of corrective saccade amplitudes to main saccade amplitude associated with the subjects eye movement to each fixation target presented to the subject. The corrective saccade measurements can include measurements for a first corrective saccade and at least a second corrective saccade and the corrective saccade measurements for each corrective saccade includes at least one of latency, amplitude, accuracy and velocity of each respective corrective saccade.

This VOG system used in the method of the present invention may provide an objective tool for assisting in the diagnosis of Traumatic Brain Injury, Progressive Supernuclear Palsy (PSP) and other degenerative cerebellar disorders that cause highly saccadic results. Some of the above objects are achieved with a goggle based VOG system that objectively calculates, and displays main and possibly secondary and higher saccades results to assist in the diagnosis of Internuclear Opthalmoplegia (INO). The system may further assist in the diagnosis of Internuclear Opthalmoplegia (INO) for each eye or for bilateral diagnosis. Some of the above objects are achieved with a goggle based VOG system that objectively calculates, and displays main and possibly secondary and higher saccades results to assist in the diagnosis of Ocular Lateral Pulsion. Some of the above objects are achieved with a goggle based VOG system that objectively calculates, and displays main and possibly secondary and higher saccades results to assist in the diagnosis of Glissades eye movements.

These and other advantages of the present invention will be clarified in the description of the preferred embodiments taken together with the attached drawings.

Some of the above objects are achieved with a goggle based VOG system that calculates, and displays secondary, and higher, corrective saccades. This VOG system provides an objective tool for assisting in the diagnosis of Progressive Supernuclear Palsy (PSP) and other degenerative cerebellar disorders that cause highly saccadic results.

Some of the above objects are achieved with a goggle based VOG system that objectively calculates, and displays main and possibly secondary and higher saccades results to assist in the diagnosis of Internuclear Opthalmoplegia (INO). The system may further assist in the diagnosis of Internuclear Opthalmoplegia (INO) for each eye or for bilateral diagnosis.

Some of the above objects are achieved with a goggle based VOG system that objectively calculates, and displays main and possibly secondary and higher saccades results to assist in the diagnosis of Ocular Lateral Pulsion.

Some of the above objects are achieved with a goggle based VOG system that objectively calculates, and displays main and possibly secondary and higher saccades results to assist in the diagnosis of Glissades eye movements.

These and other advantages of the present invention will be clarified in the description of the preferred embodiments taken together with the attached drawings.

DESCRIPTION OF THE PREFERRED EMBODIMENTS

Figure 1:
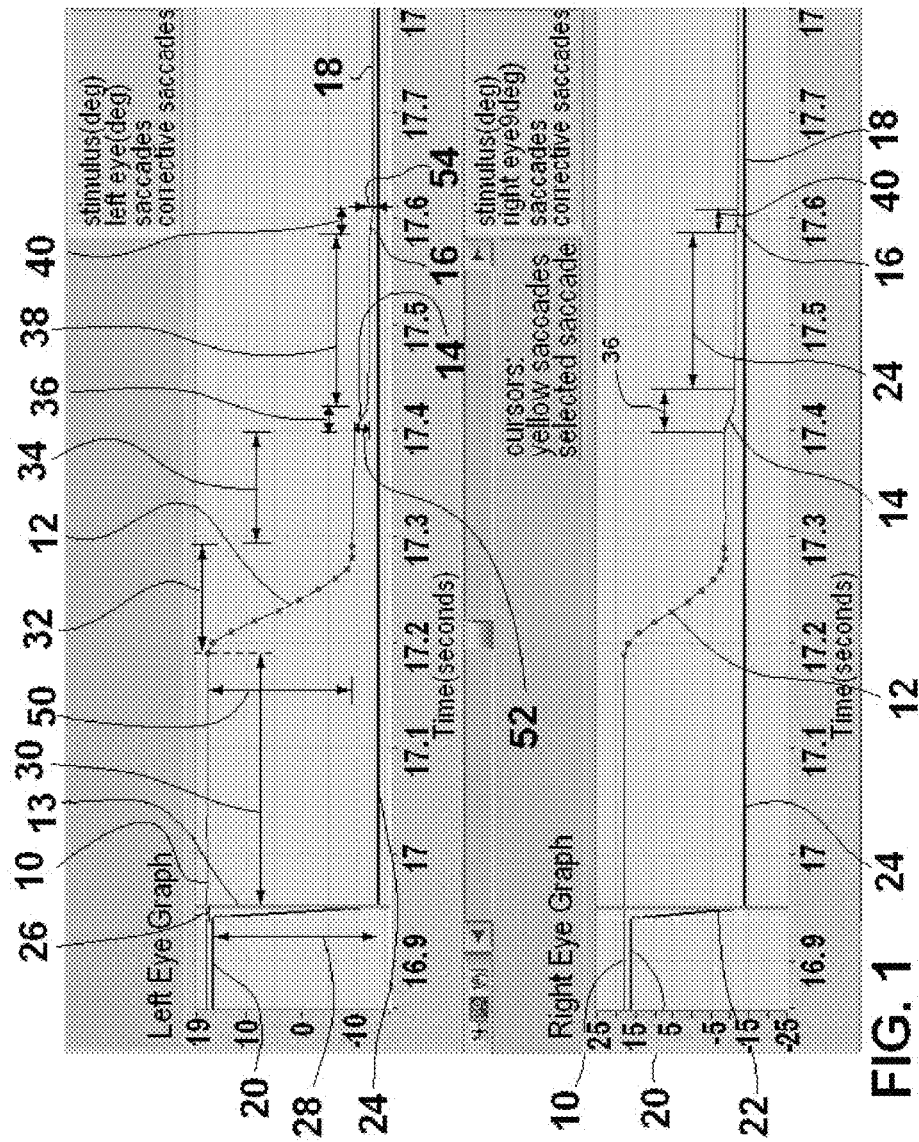
FIGS. 1 and 2 are schematic views of left and right eye traces of collected data for the calculation of corrective saccade measurements from the eye data in a VOG system in accordance with the present invention.

The present invention uses a portable, head mounted, digital camera based, video oculography (VOG) system such as the I-PORTAL® brand VOG systems from Neuro-Kinetics, Inc (NKI). The I-PORTAL® brand VOG systems from Neuro-Kinetics, Inc are fully digital VOG systems that delivers accurate 4D eye tracking recordings. The lightweight goggle system is offered in standard 60 Hz and high-speed 120 Hz goggle sets in the I-PORTAL® brand VOG systems, both in occluded and free field of view. Similar VOG systems for implementing the present invention are described in U.S. Patent Application Publications 2005-0099601, 2007-0132841, 2008-0049186, and 2008-0049187 which are incorporated herein by reference in their entirety. The speed and resolution of the cameras may be further modified in this system with replacement of these digital cameras with available higher speed digital cameras. The modular nature of the I-PORTAL® brand VOG system allows this customization to be easily accommodated with minimal software accommodations.

The video oculography based system for the subject must be configured to collect eye images of the patient in excess of (at a minimum) 60 hz and configured to resolve eye movements smaller than (at a minimum) at least 3 degrees of motion. Increasing the frame rate and resolution improves the meaningful data obtained in the present invention particularly when reviewing higher order corrective saccades. A video oculography based system for the subject configured to collect eye images of the patient in excess of 70 hz and configured to resolve eye movements smaller than at least 2 degrees of motion should provide meaningful results, while video oculography based system for the subject configured to collect eye images of the patient in excess of 75 hz, or even 100 hz and configured to resolve eye movements smaller than at least 1 degrees of motion is better. A video oculography system configured to collect eye images of the patient in excess of 200 hz and configured to resolve eye movements smaller than at least 0.1 degrees of motion is believed to be highly effective and easily obtainable through the customizable I-PORTAL® brand VOG system from NKI.

All of the above identified VOG systems include a goggle head mounted system with at least one, and typically two, digital camera(s) trained on the subjects eyes. Each camera is generally connected to, and may even be powered by, a computer, such as through a "firewire" type connection. The computer may be a laptop portable computer. The digital cameras may allow for digital centering of the patients pupil at least in one direction through concentrating on the region of interest, and possibly in two directions (X and Y). The use of digital centering eliminates the need for a mechanical adjustment mechanism (e.g. a slide) in the given direction.

The VOG system of the present invention is designed to track and record 4-D movement of the eye, which is generally movement in an X-Y plane, pupil dilation and eye rotation or torsion about the line of sight. The construction of this type of goggle based VOG system is believed to be known to one of ordinary skill in the art. The video oculography based system for the subject must be configured to collect eye images of the patient in excess of 200 hz and configured to resolve eye movements smaller than (at a minimum) at least 0.1 degrees of motion.

The present invention provides for collecting eye data with the head mounted google based video oculography based system wherein at least one, and generally a plurality of, fixation target is (are) presented to the subject, with each target in a defined position configured to yield a voluntary saccadic eye response from at least one eye of the patient. A laser that can project an image anywhere within the user's field of vision (generally +-sixty degrees) is a suitable cost effective and accurate target generation mechanism. It is critical to know where the target is being projected relative to an original eye position. A suitable target generation mechanism is the PURSUIT TRACKER™ image creating device from NKI.

The present invention provides for calculating corrective saccade measurements from the eye data. The corrective saccade measurements may be more easily understood with a review of eye traces of such data found in FIGS. 1 and 2. Line 10 represents the positional eye trace data of each eye over time. Over time the trace 10 illustrates a primary saccade movement 12 followed by a first corrective saccade 14 and a second corrective saccade 16 prior to reaching a final fixation position 18. Higher secondary saccades (third, forth, etc) 16' may also be recorded prior to the patients reaching a final fixation position.

Although not shown, it is also possible for a subject to not reach a final fixation position 18 as shown and the patient can exhibit repeated under and over shoot continuing secondary saccade. In such a case the variability can be noted to the clinician and an average final position 18 be used for calculations wherein the average final position is calculated after the amplitude 54 of subsequent secondary saccades 16' fail to decrease.

Figure 2:
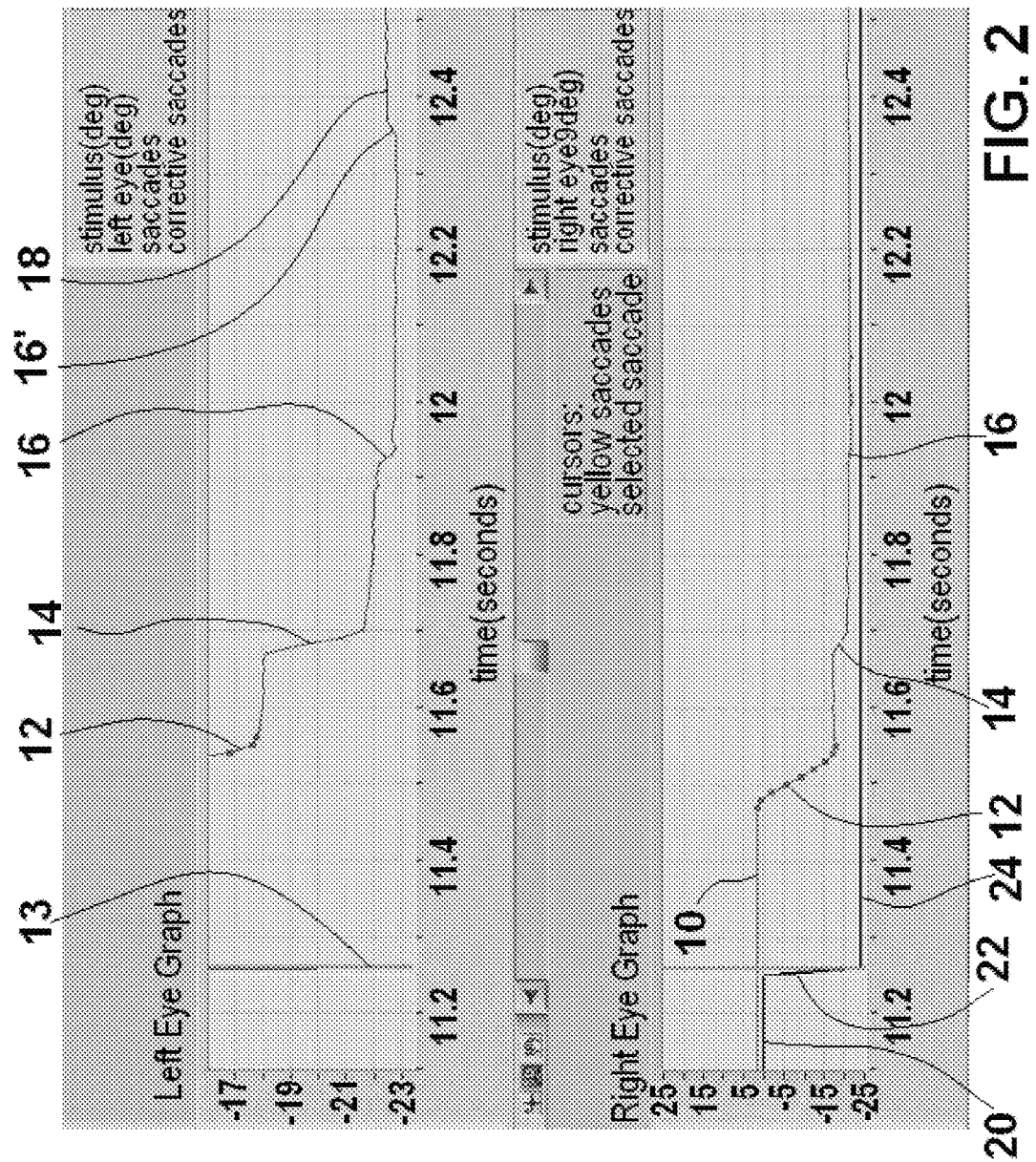

The graph of FIG. 1 also shows the positional trace 20 of the laser forming the fixation targets. The trace 20 is rapidly moved, shown at 22, to a defined position 24 configured to yield a voluntary saccadic eye response. The trace 20 also illustrates the time 26 of the movement and, more significantly, the amplitude 28 of the movement. The velocity of the laser movement is easily calculated as amplitude 28 divided by time 26, but this particular velocity is not likely to provide meaningful ocular response information unless the velocity becomes low (which may affect latency measurements). The end of movement 22 marks a start time 13 for the particular fixation target represented at 24.

It is important to note that the traces do not show the direction of the movement 22 from the starting location. The movements 22 will typically be performed in vertical movements, both up and down relative to a fixed starting point, horizontal movements both left and right, and combinations thereof. Further a combination movement can generate or be broken down into a pair of responses broken down into vertical and horizontal components of the target movement and the eye responses. Further it is expected that the starting locations can be throughout the user's field of vision. As the VOG system can easily accommodate and track such distinct movements in differently defined directions, they are not elaborated further herein, in order to keep this explanation clear and concise. However, it is expected that subjects can exhibit considerable directional variations in saccadic response, and such directional differences may be used as objective diagnostic tools.

The trace also shows latency 30 of the primary saccade 12, which is the time from the start 13 of the fixation target 24 till the beginning of the primary saccade 12. This is often referenced as the reaction time for the eye movement. The primary saccade time 32 represents the time of the movement of the eye during the primary saccade 12. The first corrective saccade latency 34 is the time from the end of the primary saccade movement 12 till the beginning of the first corrective saccade 14. The first corrective saccade time 36 represents the time of the movement of the eye during the first corrective saccade 14. The second corrective saccade latency 38 is the time from the end of the first corrective saccade movement 14 till the beginning of the second corrective saccade 16. The second corrective saccade time 40 represents the time of the movement of the eye during the second corrective saccade 16. Third and higher order corrective saccade 16' will include similar latency and time measurements.

The trace also shows the primary saccade amplitude 50 of the primary saccade 12, which is a measurement of the magnitude (in degrees) of the eye movement during the primary saccade 12. The trace further shows the first corrective saccade magnitude 52 of the first corrective saccade 14 and the secondary corrective saccade magnitude 54 of the secondary corrective saccade 16. Magnitudes of higher order corrective saccades, if present, would also be shown.

The present invention provides a number of objective corrective saccade analysis including a total number of corrective saccades associated with the subjects eye movement to each fixation target presented to the subject. The total number of corrective saccades for a given fixation is simply the number of corrective saccades until a final position 18 is reached. In the event no actual final position is reached it will be the number of corrective saccades until no substantive decrease in subsequent corrective saccade magnitudes is observed.

The present invention provides an objective corrective saccade analysis including a first corrective saccade latency 34 and amplitude 52 associated with the subject's first corrective saccade eye movement to each fixation target presented to the subject as described above and shown in the trace.

The present invention provides an objective corrective saccade analysis including a second (and higher) corrective saccade latency 38 and amplitude 54 associated with the subject's second (and higher) corrective saccade eye movement to each fixation target 24 presented to the subject as described above and shown in the trace.

The present invention provides an objective corrective saccade analysis including a first corrective saccade accuracy associated with the subject's first corrective saccade eye movement to each fixation target 24 presented to the subject. The first corrective accuracy is effectively calculated as the total of the primary saccade amplitude 50 plus the first corrective saccade amplitude 52 divided by the target amplitude 28. This accuracy is also a measurement of first corrective saccade overshoots (accuracy calculations greater than 1) and first corrective saccade undershoots (accuracy calculations less than 1).

The present invention provides an objective corrective saccade analysis including a first corrective saccade velocity associated with the subject's first corrective saccade eye movement to each fixation target 24 presented to the subject, which is calculated as the first corrective saccade amplitude 52 divided by the first corrective saccade time 36.

The present invention provides an objective corrective saccade analysis including a ratio of first corrective saccade amplitude 52 to main saccade amplitude 50 associated with the subject's eye movement to each fixation target 24 presented to the subject. This can be a weighting factor or consideration for considering initial latency and total latency in evaluating reaction time and other parameters of the subject. The present invention provides an objective corrective saccade analysis including a ratio of total of corrective saccade amplitudes (52+54+additional, if any) to main saccade amplitude 50 associated with the subject's eye movement to each fixation target presented to the subject.

There can obviously be other corrective saccade parameters available from the data obtained in the present invention that researchers and clinicians find useful for particular purposes, such as ratios of relative saccadic velocities, ratios of the latencies and the like. The above identified parameters are believed to provide objective meaningful data from a relatively simple and time efficient testing battery.

The present invention provides an objective corrective saccade analysis including wherein the corrective saccade measurements are calculated for the subjects left and right eyes for each fixation target presented to the subject. Further, a average corrective saccade measurements are calculated for each fixation target presented to the subject based upon an average of the left and right eye responses.

Figure 3:
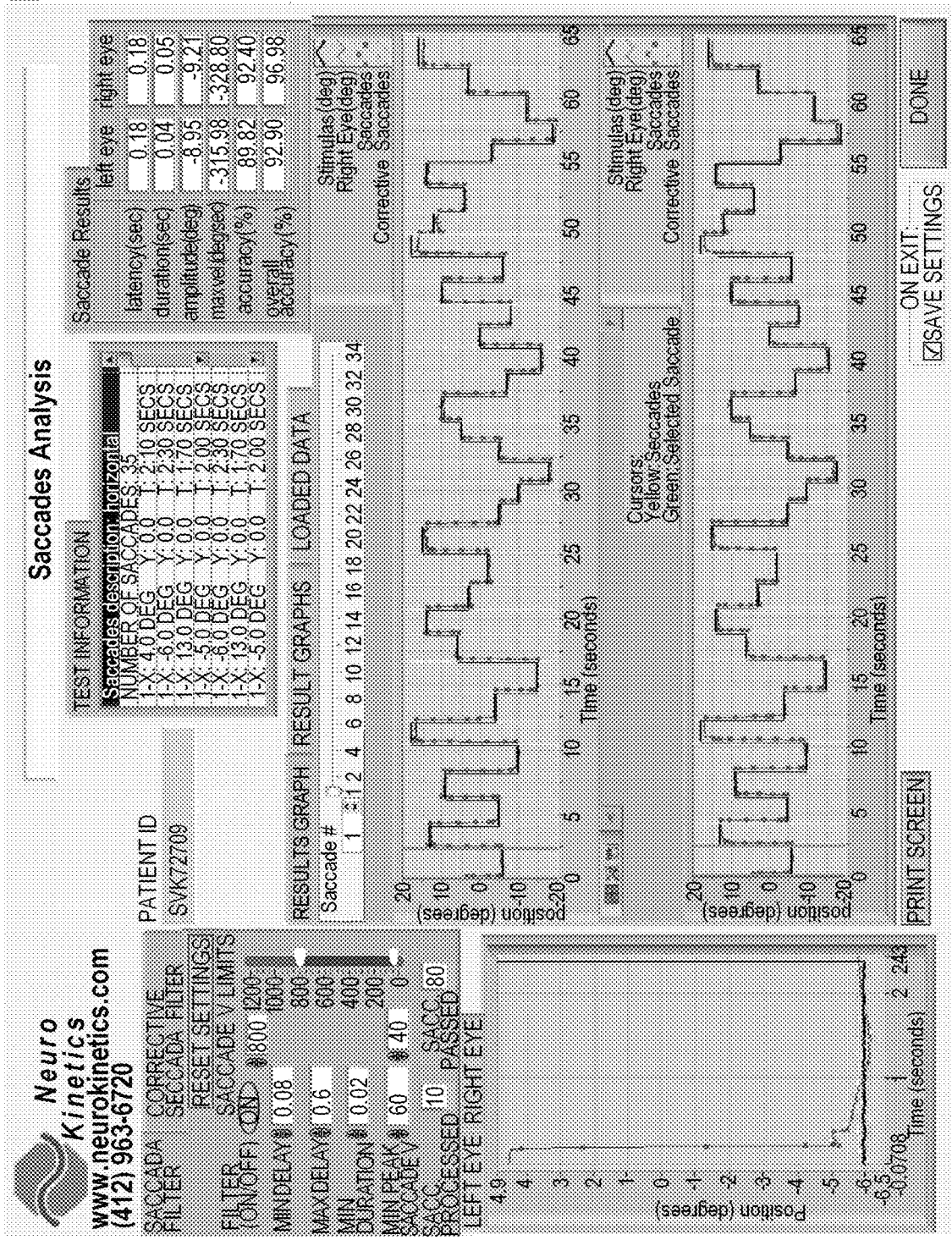
FIGS. 3 and 4 are schematic views of main saccades and a secondary corrective saccades analysis displays in a VOG system in accordance with the present invention.
Figure 4:
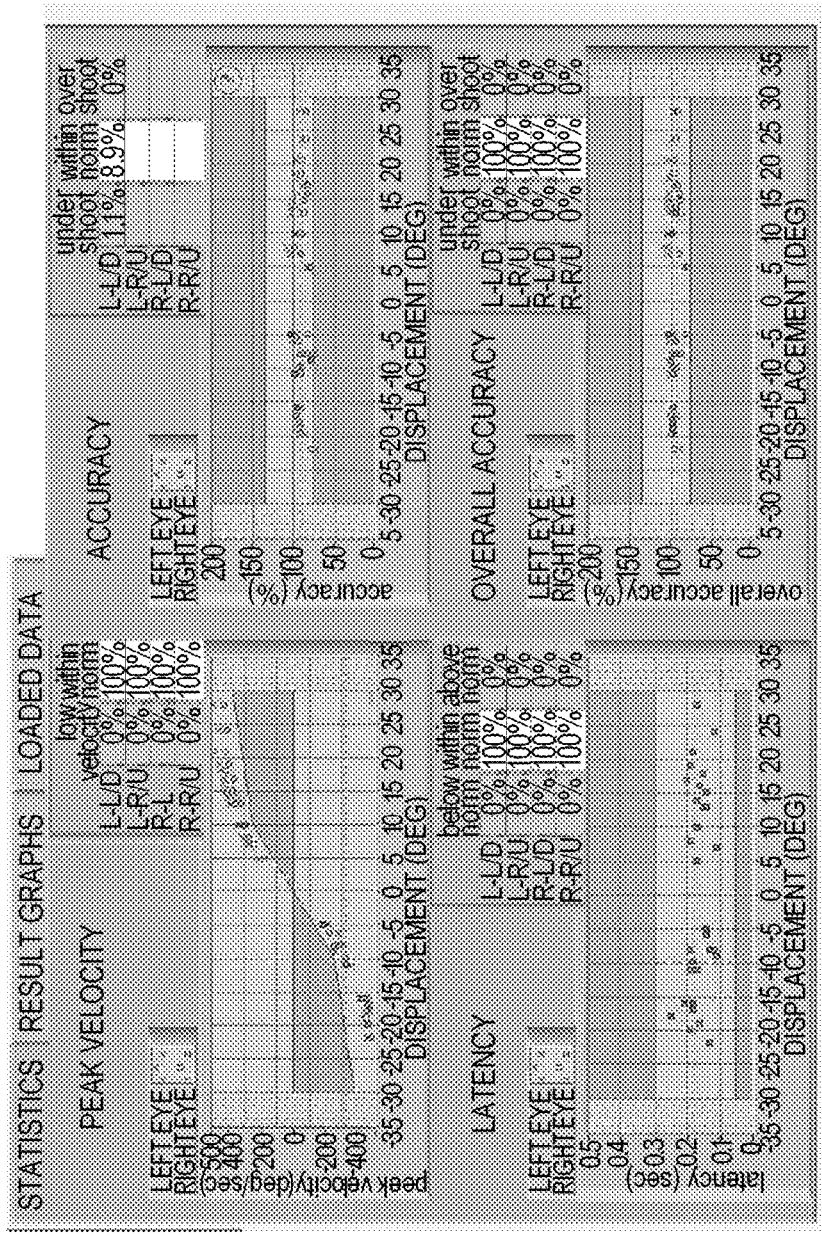

FIGS. 3 and 4 represent screenshots of potential graphic and numerical displays for the calculated parameters, however a wide variety of preferably user adjustable display formats are contemplated. A combination of graphical and numerical listings of selectable parameters is believed to be most useful.

Another addition to the simple ocular testing shown is to include a user input device, such as a button or a joystick, in which the user can indicate when the new target is seen by the user. This input would be shown as a line similar to 13 at the point when the input is recorded. This would allow for a mechanical or reflex latency measurement to be easily added to the available parameters. A joystick would allow directional inputs (up, down, left and right) which could be used to minimize anticipatory inputs as the direction of the joystick input would need to match the direction of the target 24 from the start for a valid reflex input. Comparing the reflex latency to the ocular reflex time is a further useful tool to researchers and clinicians Traumatic Brain Injury (TBI)

Objective measurement of Traumatic Brain Injuries (TBI), such as concussions, is not readily available to researchers or clinicians. The corrective saccade parameters that are provided with the method and apparatus of the present invention are believed to assist in forming objective indicators of TBI.

First, subjects that have a pre-TBI baseline under the present invention can use these results to test later to see if there is a potential for TBI due to intervening injury or trauma. Substantial variation in a subjects results from a their own baseline results for total number of corrective saccades, first corrective saccade latency, first corrective saccade amplitude, first corrective saccade accuracy associated with the subject's first corrective saccade eye movement to each fixation target presented to the subject, first corrective saccade velocity, ratio of first corrective saccade amplitude to main saccade amplitude, or ratio of total of corrective saccade amplitudes to main saccade amplitude could be used as TBI indicators, individually, or more likely collectively.

However it is anticipated that a normative database of corrective saccade parameters for the relevant populations (e.g. high school athletes) could be used to form an "aggregate baseline" and a subjects post trauma results compared to the aggregate base line to determine if TBI is seen as likely or a possibility, even if the patient were never previously tested.

Internuclear Opthalmoplegia (INO)

Internuclear ophthalmoplegia (INO) is a disorder of conjugate lateral gaze in which the affected eye shows impairment of adduction. The disorder is caused by injury or dysfunction in the medial longitudinal fasciculus (MLF), a heavily-myelinated tract that allows conjugate eye movement. In young patients with bilateral INO, Multiple Sclerosis often the cause. In older patients with one-sided lesions a stroke is a distinct possibility. However, there is a long list of possible causes. Currently, audiologists are diagnosing INO through direct observation of the patient or of a recording of the patient (i.e. a trace of eye position.

In the VOG system of the present invention an objective measure of patient corrective saccadic response is obtained to provide an objective tool for INO diagnosis in patients. Namely the saccades eye movements of the patient are calculated for each eye, including the calculation of the main saccades and secondary corrective saccades. The details of the analysis are described in connection with FIGS. 1-2. The saccades calculations include calculations for over and under shoots, latency, accuracy, velocity, and comparison of such values to the other eye results in bilateral calculations. The subsequent corrective saccades following the secondary are similarly calculated.

With regard to the diagnosis of INO these objective measurements provide an objective tool for such diagnosis. Comparison of the main saccades measurements, and possibly the secondary and higher corrective saccade, to threshold measurements relative to the target and the other eye response will provide indication of INO diagnosis. The particular thresholds established may vary with age and other physiologic parameters of the patients as will be understood by those of ordinary skill in the art. The calculation of the INO diagnosis may include ranges of results for the patients, such as a result of "INO highly likely", "INO possible" and "INO not indicated". Alternatively a numerical scaled result can be given on a preset scale to give numerical results as desired.

Ocular Lateral Pulsion (OLP)

Ocular Lateral Pulsion (OLP) is caused by infarcts in the distribution of the posterior inferior cerebellar artery or distribution of the superior cerebellar artery. With regard to the diagnosis of OLP the objective saccade eye movement of a goggle based VOG system provide an objective tool for diagnosis of OLP.

Comparison of the main saccades measurements, and possibly the secondary and higher corrective saccade, to threshold measurements relative to the target and the other eye response will provide indication of OLP diagnosis. The particular thresholds established may vary with age and other physiologic parameters of the patients as will be understood by those of ordinary skill in the art. The calculation of the OLP diagnosis may include ranges of results for the patients, such as a result of "OLP highly likely", "OLP possible" and "OLP not indicated". Alternatively a numerical scaled result can be given on a preset scale to give numerical results as desired.

Glissades Eye Movements

Glissades eye movements are when eye velocity slows just prior to reaching the eye target and the eye gradually acquires the target or steps with a small additional saccade. Glissades eye movements can be caused by a cerebellar disorder, eye muscle or nerve weakness or head movement during the test. Current diagnosis is through visual inspection of patient eye response. With regard to the diagnosis of glissades eye movement the objective saccade eye movement of a goggle based VOG system provide an objective tool for diagnosis of glissades eye movement.

Comparison of the main saccades measurements, and possibly the secondary and higher corrective saccade, to threshold measurements relative to the target and the other eye response will provide indication of glissades eye movement diagnosis. The particular thresholds established may vary with age and other physiologic parameters of the patients as will be understood by those of ordinary skill in the art. The calculation of the glissades eye movement diagnosis may include ranges of results for the patients, such as a result of "glissades eye movement highly likely", "glissades eye movement possible" and "glissades eye movement not indicated". Alternatively a numerical scaled result can be given on a preset scale to give numerical results as desired.

Progressive Supernuclear Palsy

Additionally the measurement and display of secondary, and higher, corrective saccades may further include objective diagnosis of associated diseases for the secondary saccades may be indicative. These include Progressive Supernuclear Palsy (PSP) and other degenerative cerebellar disorders that cause highly saccadic results.

Progressive supranuclear palsy (PSP) is a rare brain disorder that causes serious and permanent problems with control of gait and balance. The most obvious sign of the disease is an inability to aim the eyes properly, which occurs because of lesions in the area of the brain that coordinates eye movements. Some patients describe this effect as a blurring. PSP patients often show alterations of mood and behavior, including depression and apathy as well as progressive mild dementia. Initial complaints in PSP are typically vague and an early diagnosis is always difficult. PSP is often misdiagnosed because some of its symptoms are very much like those of Parkinson's disease, Alzheimer's disease, and rarer neurodegenerative disorders, such as Creutzfeldt-Jakob disease. In fact, PSP is most often misdiagnosed as Parkinson's disease early in the course of the illness. Memory problems and personality changes may also lead a physician to mistake PSP for depression, or even attribute symptoms to some form of dementia. The key to diagnosing PSP is identifying early gait instability and difficulty moving the eyes, the hallmark of the disease, as well as ruling out other similar disorders, some of which are treatable. The present invention can greatly improve proper and early PSP diagnosis.

Similar to the above diagnostic tools, comparison of the main saccades measurements, and generally the secondary and possibly higher corrective saccades, to threshold measurements relative to the target and the other eye response will provide indication of PSP diagnosis. The particular thresholds established may vary with age and other physiologic parameters of the patients as will be understood by those of ordinary skill in the art. The calculation of the PSP diagnosis may include ranges of results for the patients, such as a result of "PSP highly likely", "PSP possible" and "PSP not indicated". Alternatively a numerical scaled result can be given on a preset scale to give numerical results as desired.

In short the present invention provides a tool for clinicians, researchers, caregivers, and educators (and even manufacturers) that can be used in a number of distinct applications and although the present invention has been described with particularity herein, the scope of the present invention is not limited to the specific embodiment disclosed. It will be apparent to those of ordinary skill in the art that various modifications may be made to the present invention without departing from the spirit and scope thereof. The scope of the invention is not to be limited by the illustrative examples described above.

What is claimed is:

1. A method of objective diagnostic of Internuclear ophthalmoplegia in a subject comprising the steps of:
   A) Collecting eye data of the subject with an eye tracking system wherein at least one fixation target is presented to the subject in a defined position configured to yield a voluntary saccadic eye response from the eyes of the patient, wherein the initial saccadic eye response to the target is a primary saccadic response and subsequent saccadic eye responses to the target are corrective saccadic eye responses to the target;
   B) Calculating primary saccadic response measurements and corrective saccade measurements from the eye data;
   C) Comparing at least one of the primary saccades response measurements of each eye to the same primary saccades response measurement of other eye;
   D) Comparing at least one of the corrective saccadic eye response measurements of each eye to the same corrective saccadic eye response measurement of other eye; and
   E) Utilizing the comparison of steps C and D as an indication of the presence of Internuclear ophthalmoplegia in a subject.

2. The method of objective diagnostic of Internuclear ophthalmoplegia in a subject according to claim 1 wherein the eye tracking system is a video oculography system configured to collect eye images of the patient.

3. The method of objective diagnostic of Internuclear ophthalmoplegia in a subject according to claim 1 wherein average corrective saccade measurements are calculated for each fixation target presented to the subject based upon an average of the left and right eye responses.

4. The method of objective diagnostic of Internuclear ophthalmoplegia in a subject according to claim 1 further comprising the step of displaying the collected eye data from each fixation target as an eye movement trace graphing angular movement of the subject eye over time relative to the position of the fixation target.

5. The method of objective diagnostic of traumatic brain injury in a subject according to claim 1 wherein the corrective saccade measurements include measurements for a first corrective saccade and at least a second corrective saccade.

6. The method of objective diagnostic of Internuclear ophthalmoplegia in a subject according to claim 1 wherein the corrective saccade measurements for each corrective saccade includes at least one of latency, amplitude, accuracy and velocity of each respective corrective saccade.

7. The method of objective diagnostic of Internuclear ophthalmoplegia in a subject according to claim 1 wherein at least one fixation target is formed by a laser configured to display a visible target at any point in the patients field of vision.

8. A method of objective diagnostic of at least one of Internuclear ophthalmoplegia, Ocular Lateral Pulsion, Glissades Eye Movements and Progressive Supernuclear Palsy in a subject comprising the steps:
   A) Collecting eye data of the subject with an eye tracking system wherein at least one fixation target is presented to the subject in a defined position configured to yield a voluntary saccadic eye response from the eyes of the patient, wherein the initial saccadic eye response to the target is a primary saccadic response and subsequent saccadic eye responses to the target are corrective saccadic eye responses to the target;
   B) Calculating primary saccadic response measurements and corrective saccade measurements from the eye data;
   C) Comparing at least one of: i) at least one of the primary saccades response measurements of each eye to threshold measurements relative to the target, and ii) at least one of the primary saccades response measurements of each eye to the same primary saccades response measurement of other eye;
   D) Comparing at least one of: i) at least one of the corrective saccadic eye response measurements of each eye to threshold measurements relative to the target, and ii) at least one of the corrective saccadic eye response measurements of each eye to the corrective saccadic eye response measurement of other eye; and
   E) Utilizing the comparison of steps C and D as an indication of the presence of at least one of Internuclear ophthalmoplegia, Ocular Lateral Pulsion, Glissades Eye Movements and Progressive Supernuclear Palsy in a subject.

9. The method of objective diagnostic in a subject according to claim 8 wherein the comparison of steps C and D is utilized as an indication of the presence of at least Internuclear ophthalmoplegia.

10. The method of objective diagnostic in a subject according to claim 8 wherein the comparison of steps C and D is utilized as an indication of the presence of at least Ocular Lateral Pulsion.

11. The method of objective diagnostic in a subject according to claim 8 wherein the comparison of steps C and D is utilized as an indication of the presence of at least Glissades Eye Movements.

12. The method of objective diagnostic in a subject according to claim 8 wherein the comparison of steps C and D is utilized as an indication of the presence of at least Progressive Supernuclear Palsy.

13. The method of objective diagnostic in a subject according to claim 8 wherein the corrective saccade measurements include measurements for a first corrective saccade and at least a second corrective saccade.

14. The method of objective diagnostic in a subject according to claim 8 wherein the corrective saccade measurements for each corrective saccade includes at least one of latency, amplitude, accuracy and velocity of each respective corrective saccade.

15. A method of measuring ocular response in a subject comprising the steps of:
   Providing an eye tracking system for the subject configured to collect eye images of the patient;
   Collecting eye data with the eye tracking system wherein a plurality of fixation targets are presented to the subject each in a defined position configured to yield a voluntary saccadic eye response from at least one eye of the patient, wherein the initial saccadic eye response to the target is a primary saccadic response and subsequent saccadic eye responses to the target are corrective saccadic eye responses to the target;

Calculating corrective saccade measurements from the eye data, wherein the corrective saccade measurements include measurements for a first corrective saccade and at least a second corrective saccade and the corrective saccade measurements for each corrective saccade includes at least one of latency, amplitude, accuracy and velocity of each respective corrective saccade, wherein the corrective saccade measurements from the eye data is used as an objective diagnostic tool for at least one of Internuclear Opthalmopligia, Ocular Lateral Pulsion, and Progressive Supernuclear Palsy And Glissades.

16. The method of measuring ocular response in a subject according to claim 15 wherein the eye tracking system is a video oculography system configured to collect eye images of the patient in excess of 200 hz.

17. The method of measuring ocular response in a subject according to claim 15 wherein the corrective saccade measurements are calculated for the subjects left and right eyes for each fixation target presented to the subject.

18. The method of measuring ocular response in a subject according to claim 17 wherein average corrective saccade measurements are calculated for each fixation target presented to the subject based upon an average of the left and right eye responses.

19. The method of measuring ocular response in a subject according to claim 15 further comprising the step of displaying the collected eye data from each fixation target as an eye movement trace graphing angular movement of the subject eye over time relative to the position of the fixation target.

20. The method of measuring ocular response in a subject according to claim 15 wherein the corrective saccade measurements from the eye data include a total number of corrective saccades associated with the subjects eye movement to each fixation target presented to the subject.

* * * * *